United States Patent [19]

Gerling et al.

[11] Patent Number: 5,089,492
[45] Date of Patent: Feb. 18, 1992

[54] PHARMACEUTICALS AND DIETETICS CONTAINING ACYLAMINO ACID DERIVATIVES

[75] Inventors: Klaus Gerling, Laatzen; Henning Heinemanmn, Lehrte OT Aligse; Andreas Meier, Hemmingen; Klaus Langer, Erlangen, all of Fed. Rep. of Germany

[73] Assignees: Kali-Chemie AG, Hanover; Pfrimmer Kabi GmbH & Co. KG, Erlangen, both of Fed. Rep. of Germany

[21] Appl. No.: 527,844

[22] Filed: May 24, 1990

[30] Foreign Application Priority Data

Jun. 1, 1989 [DE] Fed. Rep. of Germany ....... 3917880

[51] Int. Cl.$^5$ ............................................ A61K 31/395
[52] U.S. Cl. .................................. 514/210; 514/315; 514/326; 514/422; 514/423; 514/449; 514/450; 514/452; 514/467; 514/549; 514/551; 514/563; 514/616; 546/207; 546/226; 546/245; 548/344; 548/517; 548/540; 548/953; 549/347; 549/372; 549/450; 549/510; 560/170; 562/560; 562/561; 562/562; 562/564; 562/567; 564/159
[58] Field of Search ............... 560/170; 562/561, 562, 562/560, 564, 567; 564/158, 159; 548/344, 517, 540, 953; 549/347, 372, 450, 510; 546/207, 226, 245; 514/210, 315, 326, 422, 423, 450, 452, 449, 403, 467, 549, 551, 563, 616

[56] References Cited

FOREIGN PATENT DOCUMENTS 2556593 6/1985 France .
WO88/09789 12/1988 PCT Int'l Appl. .

OTHER PUBLICATIONS

McGregor, Chem. Abst., 57:1234i-1234h (1962).
Harada, Chem. Abst., 100:103,835p (1983).
Steglich, Chem. Abst., 89:214,864w (1978).
Ojima, Chem. Atst., 95:187,642n (1981).
J. H. Close, N. Engl. J. Med. 290, pp. 663–667 (1974).
M. E. Tischler, M. Desautels, A. L. Goldberg, J. Biol.--Chem. 257, pp. 1613–1621 (1982).
G. Francois et al., Clin Nutr. 3, pp. 99–101 (1984).
E. McOmie, "Protective Groups in Organic Chemistry", Plenum Press (1973).

*Primary Examiner*—Michael L. Shippen
*Attorney, Agent, or Firm*—Foley & Lardner

[57] ABSTRACT

Acylamino carboxylic acid derivatives corresponding to the formula I

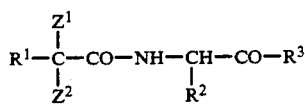

in which the groups $R^1$, $R^2$, $R^3$, $Z^1$ and $Z^2$ represent functional groups specified in the claims. The acylamino carboxylic acid derivatives have valuable pharmacological properties which, in particular, favorably influence nitrogen metabolism. The compounds are useful as active ingredients in pharmaceutical and/or dietetic compositions for treatment or prevention of nitrogen metabolism disturbances in large mammals caused, for example, by liver or kidney damage.

13 Claims, No Drawings

PHARMACEUTICALS AND DIETETICS CONTAINING ACYLAMINO ACID DERIVATIVES

BACKGROUND OF THE INVENTION

The present invention relates to new acylamino acid derivatives with valuable pharmacological properties, especially properties favorably affecting nitrogen metabolism, to the use of these acylamino acid derivatives as pharmaceuticals and dietetics, especially for the treatment and prophylaxis of, for example, disturbances of nitrogen metabolism caused by liver and/or kidney damage in relatively large mammals, especially humans, to pharmaceuticals and dietetics which contain acylamino acid derivatives as active ingredients, and to the preparation of the acylamino acid derivatives.

It is known that the corresponding α-keto analogs of essential amino acids are possible substitutes for the essential amino acids. After enzymatic transamination, the α-keto analogs are, with a few exceptions, available as building blocks for proteins in the body (J. H. Close, N. Engl. J. Med. 290 (1974), pp. 663-667).

Leucine and its α-keto analog 4-methyl-2-oxovaleric acid (α-ketoleucine) play a special part in protein synthesis because the modes of action of the two substrates complement each other synergistically. On the one hand, protein synthesis is stimulated by leucine, and on the other hand, protein breakdown is inhibited by α-ketoleucine (M. E. Tischler, M. Desantels, A. L. Goldberg, J. Biol.-Chem. 257 (1982), pp. 1613-1621).

Furthermore, nitrogen is consumed in the synthesis of α-amino acids from their corresponding α-keto analogs in the body, which leads additionally to a reduction in the amount of nitrogen compounds excreted in the urine.

This knowledge has been applied by utilizing the effects of α-keto and α-amino acids in a wide variety of metabolic situations, especially in catabolic states as occur in connection with hepatic and renal insufficiencies, trauma, sepsis and fasting states.

Compositions which contain α-amino carboxylic acids and α-keto analogs of amino carboxylic acids are disclosed, for example, in French Patent Application No. FR 2,556,593 or are already marketed in the form of preparations for oral administration, such as, for example, the commercial product ULTRAMINE (manufactured by Pfrimmer).

Although these products have been used successfully in therapy, there are still various problems associated both with their manufacture and with their oral and parenteral use. Thus, for example, when administered orally, these amino acids and α-keto analogs are, unfortunately, not utilized optimally because of the absorption behavior.

When administered parenterally as described, for example, for leucine and ketoleucine by G. Francois et al. (Clin. Nutr., 3 (1984), pp. 99-101), the advantageous effect of a reduction in nitrogen excretion can only be achieved if substrates of carbohydrate metabolism are administered concurrently. However, infusion solutions which are manufactured to contain substrates of carbohydrate metabolism in addition to amino acids and their α-keto analogs have the disadvantage that when reducing sugars such as, for example, glucose are used, Maillard products may form in completely assembled infusion solutions either during the necessary heat sterilization or during storage.

SUMMARY OF THE INVENTION

An object of the invention is to prepare new amino acid derivatives with valuable pharmacological and dietetic properties, which permit the aforementioned disadvantages of the prior art to be overcome.

Another object of the invention is to provide new pharmaceuticals and/or dietetics which can be used in amino acid replacement therapy and for treating or preventing disturbances of nitrogen metabolism and which do not have the aforementioned disadvantages of the state of the art.

These and other objects of the invention are achieved by providing a compound corresponding to the formula I:

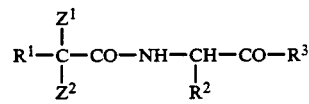

in which
$R^1$ represents an organic radical A

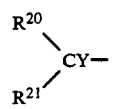

in which
Y represents hydrogen or another bond,
$R^{20}$ represents hydrogen or methyl, and
if $R^{20}$ is hydrogen, $R^{21}$ denotes isopropyl and, if $R^{20}$ is methyl, $R^{21}$ denotes methyl or ethyl,
$R^2$ represents the organic radical A'

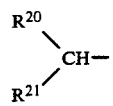

in which
$R^{20}$ and $R^{21}$ have the above meanings,
$R^3$ represents hydroxy or lower alkoxy or an amino group B

in which
$R^5$ denotes hydrogen or lower alkyl, and
$R^6$ denotes hydrogen, lower alkyl or, if $R^5$ is hydrogen,
 $R^6$ may be the deamino radical of a biogenic amino acid, or
$R^5$ and $R^6$ together with the N atom to which they are bonded form a 3- to 6-membered heterocycle, and
$Z^1$ and $Z^2$ together represent oxygen or a physiologically acceptable alkylenedioxy group $O-(CH_2)_n-O$ in which n is 1 to 4, or
$Z^1$ and $Z^2$ each represent a physiologically acceptable $R^7-O-$ group in which $R^7$ denotes lower alkyl, or $Z^1$ represents an $R^7$—O— group in which $R^7$ has the above meaning, and $Z^2$ together with Y represents a bond, or a salt thereof in which $R^3$ represents hydroxy with a physiologically acceptable cation.

DETAILED DESCRIPTION OF PREFERRED EMBODIMENTS

The invention relates to new acylamino carboxylic acid derivatives of formula I

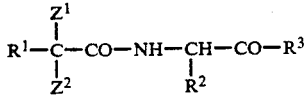

in which
$R^1$ represents an organic radical A

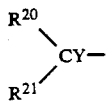

in which
Y represents hydrogen or another bond and, if $R^{20}$ is hydrogen, $R^{21}$ denotes isopropyl and, if $R^{20}$ is methyl, $R^{21}$ denotes methyl or ethyl,
$R^2$ represents the organic radical A'

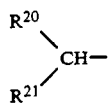

in which $R^{20}$ and $R^{21}$ have the above meanings,
$R^3$ represents hydroxy or lower alkoxy or an amino group B

in which
$R^5$ denotes hydrogen or lower alkyl,
$R^6$ denotes hydrogen, lower alkyl or, if $R^5$ is hydrogen,
$R^6$ may be the deamino radical of a biogenic amino acid, or
$R^5$ and $R^6$ together with the N atom to which they are bonded form a 3- to 6-membered heterocycle, and
$Z^1$ and $Z^2$ together represent oxygen or a physiologically acceptable alkylenedioxy group O—($CH_2$)$_n$—O in which n is 1-4, or
$Z^1$ and $Z^2$ each represent a physiologically acceptable $R^7$—O— group in which $R^7$ denotes lower alkyl, or
$Z^1$ represents an $R^7$—O— group in which $R^7$ has the above meaning, and $Z^2$ together with Y represents a bond,
and salts of those compounds of formula I in which $R^3$ represents hydroxy with a physiologically acceptable cation.

Where the substituents in the compounds of formula I represent or contain lower alkyl groups, these can be straight-chain or branched and preferably contain 1 to 4, particularly 1 to 2, carbon atoms.

In the compounds of formula I, $Z^1$ and $Z^2$ preferably together represent oxygen, so that the resulting compounds have the general formula Ia

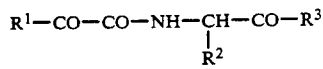

in which $R^1$ to $R^3$ have the meanings indicated above. These are referred to hereinafter as "ketopeptides".

Besides the ketopeptides of formula Ia, the invention also includes their physiologically acceptable derivatives in which the keto group is derivatized by ketal formation, that is to say, compounds of formula I in which $Z^1$ and $Z^2$ each represent a physiologically acceptable $R^7$—O— group. The lower alkyl group $R^7$ in such groups is an alkyl group with, for example, 1 to 4, particularly 2 to 3, carbon atoms, which is preferably straight chain. $R^7$ preferably represents ethyl. A diol can also be used for the ketal formation. $Z^1$ and $Z^2$ in compounds which result in this case together represent an alkylenedioxy group. In the case of cyclic ketals, those particularly preferred are the ones in which the alkylene chain contains 2 or 3 carbon atoms. The ketal derivatives of compounds of formula Ia also include compounds in which the enol form of these compounds is derivatized by ketal formation, that is to say compounds in which $Z^1$ represents an $R^7$—O— group, and $Z^2$ together with Y forms a bond. These are referred to hereinafter as "enol ether derivatives".

A radical A' present in $R^1$ and/or $R^2$ represents the radical X of a biogenic α-amino carboxylic acid X—CHNH$_2$—COOH selected from the group consisting of valine, leucine and isoleucine. Biogenic amino acids are preferably those L-α-amino carboxylic acids found in biological material. Such groups of formula A' are then the radical $(CH_3)_2CH$— derived from valine, the radical $(CH_3)_2CH$—$CH_2$— derived from leucine and the radical $CH_3$—$CH_2$—$CH(CH_3)$— derived from isoleucine.

To simplify the naming of the L-α-amino carboxylic acids the three-letter symbols recommended by the IUPAC nomenclature commission are used. The symbols used in the present application are listed in the following table.

| Amino acid | Symbol |
| --- | --- |
| Valine | Val |
| Leucine | Leu |
| Isoleucine | Ile |
| Lysine | Lys |
| Arginine | Arg |
| Histidine | His |
| Ornithine | Orn |

$R^1$ is advantageously an organic radical which can be derived in the manner described from L-amino acids selected from the group consisting of valine and leucine. $R^2$ is likewise advantageously a corresponding radical which can be derived from L-amino acids selected from the group consisting of valine and leucine.

The carbon atom to which $R^3$ is bonded in the compounds of formula I is at the oxidation state of a carboxylic acid C atom. This means that the compounds represent acids ($R^3$=OH) and their salts with physiologically acceptable cations, or their esters and amides. Acids of formula I in which $R^3$=OH and their salts with physiologically acceptable cations prove to be particularly advantageous. Examples of suitable pharmaceutically acceptable cations include metal cations such as cations of alkali metals such as sodium or potassium, alkaline earth metals such as calcium or magnesium, or zinc.

Another advantageous physiologically acceptable cation is an ammonium group C

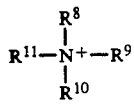

in which the substituents $R^8$ to $R^{11}$ denote, independently of one another, hydrogen or lower alkyl, or two of the substituents $R^8$ to $R^{11}$ together denote a $C_4$- or $C_5$-alkylene chain, and the other substituents denote hydrogen, or one of the radicals $R^8$ to $R^{11}$ represents the deamino radical of a basic biogenic α-amino carboxylic acid, and the other radicals denote hydrogen. Lower alkyl radicals $R^8$ to $R^{11}$ can be straight-chain or branched, but only one of the radicals can be tert. butyl, or only two of the radicals can be isoalkyl radicals. As used herein, the term "a deamino radical of a basic biogenic α-amino carboxylic acid" refers to a radical which results from a basic amino acid when the basic amino group is removed. Preferred ammonium radicals of formula C include $NH_4^+$ and ammonium ions which contain the deamino radicals of lysine, arginine, histidine or ornithine.

Where $R^3$ denotes a lower alkoxy group, this can contain 1 to 4 carbon atoms and be straight-chain or branched.

If $R^3$ denotes an amino group B, the radicals $R^5$ and $R^6$ can, independently of one another, be hydrogen or lower alkyl. Lower alkyl groups $R^5$ or $R^6$ can be straight-chain or branched and preferably contain 1-4, particularly 1-2, carbon atoms. $R^5$ and $R^6$ can also form, together with the nitrogen atom to which they are bonded, a 3- to 6-membered heterocycle. Examples of suitable heterocycles include aziridine, pyrrolidine, piperidine. It is furthermore possible, if the radical $R^5$ is hydrogen, for $R^6$ also to be the deamino radical of a biogenic amino acid. Such compounds of formula I represent tripeptide derivatives.

The naming of the ketopeptides of formula Ia and their derivatives in the present application is consistent with the IUPAC nomenclature rules using the three-letter symbols already defined above, in such a way that an α-keto carboxylic acid, which is derived from a biogenic α-amino carboxylic acid by replacing the α-amino group and the hydrogen atom bonded to the α-carbon atom with an oxo group, is named by the three-letter symbol of the base α-amino carboxylic acid being prefixed by "keto". For example, the keto analog of leucine is called "ketoleucine" (=4-methyl-2-oxovaleric acid). A ketodipeptide acid of formula Ia which is derived from ketoleucine ($R^1$=isopropylmethyl) and the amino acid valine ($R^2$=isopropyl) is called, for example, "ketoleucylvaline" or, when the configuration of the amino acid valine is also named, "ketoleucyl-L-valine". The abbreviated name is "CO—Leu—Val" or "ketoleu—Val". The corresponding methyl ester of ketoleucylvaline is accordingly, for example, "ketoleucylvaline methyl ester" and, in abbreviated form, for example, "CO—Leu—Val—OMe" or "ketoleu—Val—OMe".

Preferred compounds according to the invention are: ketoleucylleucine or ketovalylvaline, and their salts with physiologically acceptable cations of the type indicated above.

The invention also relates to the use of the compounds of formula I according to the invention as pharmaceuticals and dietetics in relatively large mammals, especially humans. The compounds according to the invention have valuable pharmacological properties, they are suitable as substitutes for essential amino acids and are distinguished, in particular, by a favorable effect on disturbances of nitrogen metabolism and good absorption and good stability in pharmaceutical preparations.

By reason of their physiological and pharmacological properties, the amino acid derivatives of formula I and their salts with physiologically acceptable cations are suitable for use as pharmaceuticals and dietetics in amino acid replacement therapy. In particular, the compounds can be used for the treatment and prophylaxis of disturbances in the nitrogen balance, for example of metabolic disorders caused by hepatic and/or renal insufficiency and catabolic disorders which may occur in connection with trauma, sepsis and fasting states.

Due to their chemical stability, even in the presence of carbohydrates, they can be incorporated in any desired manner into dietetic and/or pharmaceutical preparations and are outstandingly suitable for manufacturing infusion solutions, even infusion solutions containing reducing carbohydrates.

The invention furthermore relates to pharmaceuticals and dietetics, especially for use as amino acid substitutes and/or for the treatment and prophylaxis of disturbances of nitrogen metabolism, which contain as active ingredient compounds of formula I or their salts with a physiologically acceptable cation, in addition to customary physiologically acceptable adjuvants and/or vehicles. According to the invention, the compounds of formula I and their physiologically acceptable salts can be present together with customary pharmaceutical adjuvants and/or vehicles in solid or liquid pharmaceutical preparations. As used herein, the term "pharmaceutical compositions" is intended to refer to both to the usual pharmaceutical preparations and to dietetics. Products which can be administered orally, such as capsules, tablets, granules or coated tablets, may be mentioned as examples of solid preparations. Solid products can contain customary inorganic and/or organic pharmaceutical vehicles such as, for example, talc, starch or lactose in addition to customary pharmaceutical adjuvants, for example lubricants such as magnesium stearate or tablet disintegrating agents. Liquid products such as solutions, suspensions or emulsions can contain the customary diluents such as water and/or oils, for example triglyceride mixtures of saturated vegetable fatty acids and/or suspending agents such as, for example, polyethylene glycols and the like, or other dissolved nutrients, for example carbohydrates such as glucose. If desired, other adjuvants can be added, such as, for example, preservatives, stabilizers, flavorings and the like.

The active substances can be mixed and formulated with the pharmaceutical adjuvants and/or vehicles in a known manner. To manufacture solid drug forms, the active substances can be mixed with the vehicles and granulated wet or dry in a customary manner. Granules or powders can be used directly to fill capsules or single-portion sachets or compressed to tablet cores in a conventional manner. The latter can be coated, if desired, in a known manner.

To manufacture liquid preparations, the compounds can be dissolved or suspended in the liquid vehicle in a known manner. Solutions or suspensions intended for parenteral administration can be sterilized in a known manner.

Solutions intended for parenteral administration represent a particularly preferred embodiment of liquid preparation containing a compound of formula I, or a salt thereof with a physiologically acceptable cation, as the active ingredient. These solutions which can be administered parenterally, i.e. infusion solutions, can be manufactured in a known manner. For this purpose, the desired amount of one or more of the compounds of formula I according to the invention, or their physiologically acceptable salts, is dissolved with stirring in distilled water (for injections), ensuring exclusion of atmospheric oxygen to the maximum extent by simultaneously introducing a suitable protective gas, for example nitrogen. In the manufacture of these aqueous infusion solutions, care must be taken that the solutions are adequately isotonic. In exceptional cases (for example where the solubility is insufficient) it is also possible where appropriate to add limited amounts of known co-solvents which are miscible with water and/or other known auxiliaries for infusion solutions. The resulting solutions are subsequently pumped through a suitable series of filters with a final filter of, for example, about 0.2 μm pore diameter to remove particles and reduce the microbe count. The manufactured infusion solutions are subsequently packaged in a known manner, that is to say, for example, introduced into rinsed glass bottles, after which the headspace of these filled glass bottles is evacuated, the bottles are sealed with rubber stoppers, and finally crimp-capped. The filled and sealed bottles are then also heat-treated in an autoclave under conditions which ensure the sterility of the product.

The compounds of formula I and their physiologically acceptable salts, and pharmaceutical preparations containing them, are absorbed extremely well and, at least in part, enter the blood plasma intact even after oral administration. Their administration leads not only to a build up of favorable blood plasma concentrations of intact ketopeptides of formula Ia, but also to a distinct and long-lasting increase, in a surprising and advantageous manner, of the natural blood plasma levels of the corresponding α-amino acids and of the α-keto analogs.

Besides pharmacological advantages, the compounds of formula I and their physiologically acceptable salts also display technological advantages over corresponding mixtures of α-amino acids and α-keto acids. Acids of formula I are, for example in the form of their ornithine or lysine salts, readily soluble in water and prove to be extremely heatstable, even under extreme conditions. They can therefore be readily subjected to the heat sterilizing conditions necessary for preparing parenteral infusion solutions without decomposing. Their high long-term stability ensures that the pharmaceutical preparations of the invention have a good shelf life.

Furthermore, compared with mixtures of α-amino acids and α-keto acids, the compounds of formula I offer special advantages in the preparation of complete infusion solutions which additionally contain metabolizable carbohydrate materials. Whereas, for example, in preparing a glucose-containing, heat-sterilized solution of α-amino acids and α-keto acids, the usefulness of the sterilized solution may be impaired by Maillard reactions, Maillard reactions do not occur when compounds of formula I are processed together with glucose to produce heat-sterilized solutions.

The advantageous properties of pharmaceutical preparations containing compounds of formula I are demonstrated in the following experiments.

EXPERIMENT 1

The absorption kinetics of compounds of formula I were demonstrated using the example of ketoleucylleucine in rats. Twelve rats (Sprague Dawley, 400 g) were each given 1 g of ketoleucylleucine orally in the form of the bis-ornithate in 5% by weight glucose solution. Blood samples were taken after defined time intervals and tested for α-ketoleucylleucine, α-keto acids and α-amino acids. The results are reported in the following table:

|  | Blood Concentration in μmol/liter after | | | | | |
| --- | --- | --- | --- | --- | --- | --- |
|  | 0 min | 15 min | 30 min | 60 min | 120 min | 180 min |
| CO—Leu—Leu | 0 | 20 | 26 | 15 | 9 | 6 |
| CO—Leu | 20 | 91 | 135 | 91 | 77 | 58 |
| Leu | 185 | 715 | 795 | 715 | 715 | 610 |

The experimental results listed in the table show, using the example of oral administration of ketoleucylleucine, that at least some of the compound of formula I is absorbed intact, and that there is a drastic increase in the plasma concentration of the corresponding α-amino acid, in this example leucine, and of the corresponding α-keto acid, in this example α-ketoleucine, over an extended period.

EXPERIMENT 2

To demonstrate the surprisingly high resistance of the ketopeptides of formula Ia to the Maillard reaction, from the group of ketopeptides the magnesium salt of ketoleucylvaline (CO—Leu—Val) and the calcium salt of ketoisoleucylleucine (CO—Ile—Leu) were each tested in comparison with the mixture of the corresponding amino acids under the following conditions.

The ketopeptide—or an equimolar sample of the base amino acid for comparison—in a concentration of 1% by weight in 20% strength glucose solution is kept at a constant temperature of 121° C. for 60 minutes. The browning caused by Maillard reactions is measured by the decrease in transmission at 420 nm.

|  | % transmission at 420 nm after | | | |
| --- | --- | --- | --- | --- |
|  | 0 min | 10 min | 30 min | 60 min |
| CO—Leu—Val (Mg salt) | 97.0 | 90.5 | 77.9 | 55.6 |
| Leu + Val mixture | 100.2 | 65.6 | 12.4 | 0 |
| CO—Leu—Ile (Ca salt) | 99.5 | 95.6 | 84.2 | 62.8 |
| Leu + Ile mixture | 97.8 | 66.4 | 5 | 0 |

The results listed in the foregoing table demonstrate the greater Maillard reaction resistance of ketopeptides compared with simple mixtures of the amino acids.

EXPERIMENT 3

To test their stability, selected ketopeptides of formula Ia were heated in an aqueous medium at pH 7 under a protective nitrogen atmosphere at 121° C. for periods of time up to 60 minutes. After the time periods indicated in the table for the heat treatment, the remaining, undecomposed ketopeptide content was determined in % (relative to the initial amount of ketopeptide employed). The analysis was carried out by high resolution liquid chromatography (HPLC) with the following:

Column: Nucleosil ™ 5 C18* length=20 cm internal diameter 4.6 mm;
Eluent: 0.05 M $NaH_2PO_4$ with 50 to 60% methanol;
Detection: UV spectrophotometer at 225 nm, range 0.08.

(*Silica gel, rendered hydrophobic by $C_{18}$-alkyl radicals, for reversed phase chromatography)

The results are listed in the following table:

|  | Percentage content remaining after | | |
| --- | --- | --- | --- |
|  | 10 min | 30 min | 60 min |
| CO—Leu—Leu (Mg salt) Purity: 97.6% | 97.0% | 100% | 99.2% |
| CO—Leu—Val (Mg salt) Purity: 99.3% | 101.5% | 103.6% | 102.0% |
| CO—Ile—Leu (Ca salt) Purity: 88.5% | 100% | 100% | 99.5% |

It is evident from the test that the ketodipeptides are very stable on exposure to heat. The variations around the 100% value are within the range of accuracy of the measurement.

The compounds of formula I can be prepared in a known manner, such that a) to prepare compounds of formula Ia

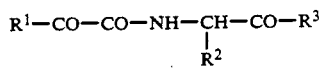

in which $R^1$, $R^2$ and $R^3$ have the above meanings, the $CZ^3Z^4$ group in compounds of formula II

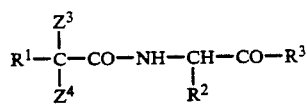

in which $R^1$, $R^2$ and $R^3$ have the above meanings, and $Z^3$ and $Z^4$ denote alkoxy or alkylthio or together represent alkylenedioxy or alkylenedithio, or in which $Z^3$ denotes alkoxy or alkylthio, and $Z^4$ together with Y represents a bond, is converted into a keto group, or b) to prepare acids of formula Ib

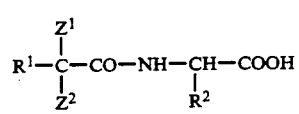

in which $R^1$, $R^2$, $Z^1$ and $Z^2$ have the above meanings, an ester of formula Ic

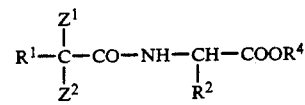

in which $R^1$, $R^2$, $Z^1$ and $Z^2$ have, the above meanings, and $R^4$ denotes lower alkyl, is hydrolyzed, or c) to prepare compounds of formula Id

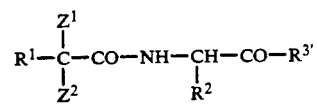

in which $R^1$, $R^2$, $Z^1$ and $Z^2$ have the above meanings, and $R^{3'}$ represents lower alkoxy or an $R^{5'}R^{6'}N$- group in which $R^{5'}$ and $R^{6'}$ have the same meanings as $R^5$ and $R^6$ with the exception of hydrogen, a compound of formula III

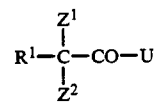

in which $R^1$, $Z^1$ and $Z^2$ have the above meanings, and U is a reactive radical, is reacted with a compound of formula IV

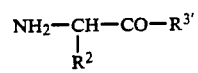

in which $R^2$ and $R^{3'}$ have the above meanings, or d) to prepare compounds of formula IE

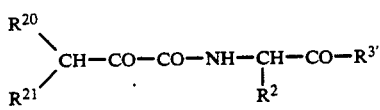

in which $R^{20}$, $R^{21}$, $R^2$ and $R^{3'}$ have the above meanings, a compound of formula V

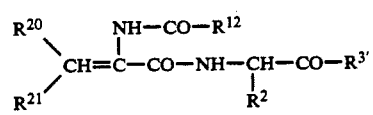

in which $R^{20}$, $R^{21}$, $R^2$ and $R^{3'}$ have the above meanings, and $R^{12}$ denotes lower alkyl, phenyl, trifluoromethyl or trichloromethyl, is cleaved, or e) an acid of formula Ib or a reactive acid derivative thereof is reacted with an amine of formula VI

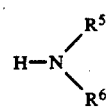

in which $R^5$ and $R^6$ have the above meanings, to yield a compound of formula If

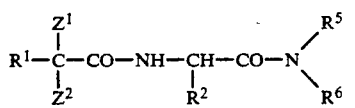

in which $R^1$, $R^2$, $R^5$, $R^6$, $Z^1$ and $Z^2$ have the above meanings, and, if desired, acids of formula Ib are converted into corresponding salts with physiologically acceptable cations, or salts of acids of formula Ib are converted into corresponding free acids.

The conversion of compounds of formula II into compounds of formula Ia by process variant a) can be carried out by conventional methods for hydrolytically cleaving ketal and enol ether groups. The hydrolytic cleavage can be carried out in an aqueous solution or suspension of the compound of formula II under acidic reaction conditions, optionally diluted with a solvent which is inert under the reaction conditions. Aqueous solutions of organic and inorganic acids are suitable for the acid hydrolysis. Organic acids which can be used for the hydrolysis include lower alkane carboxylic acids such as formic acid, acetic acid etc., haloalkane carboxylic acids such as chloroacetic acid, or organic sulfonic acids such as p-toluenesulfonic acid. Inorganic acids which can be used include mineral acids such as hydrochloric acid or phosphoric acid. Oxoketals of formula II in which $Z^3$ and $Z^4$ represent alkoxy or together represent alkylenedioxy, or $Z^3$ represents alkoxy and $Z^4$ together with Y represents a bond, are cleaved particularly well and straightforwardly by reaction with an organic or inorganic acid in aqueous medium. Dilute to concentrated aqueous mineral acids, especially hydrochloric acid, are preferably used for this. If thioketals of formula II in which $Z^3$ and $Z^4$ represent alkylthio or together represent alkylenedithio, or $Z^3$ represents alkylthio and $Z^4$ together with Y represents a bond, are to be cleaved, it is advantageous to carry out the acid hydrolysis in ethers, preferably in cyclic ethers such as dioxane. Although it is also possible to cleave the thioketal group straightforwardly by reaction with $HgO/HgCl_2/H_2O$, this route is of only minor importance for obtaining highly pure compounds suitable for pharmaceutical uses. Conversion of the ketals of formula II into compounds of formula Ia can be carried out at temperatures between room temperature and the boiling point of the solvent, with the alcohol which forms in the reaction being distilled out where appropriate.

To prepare acids of formula Ib by process variant b), esters of formula Ic can be hydrolyzed by conventional methods for hydrolyzing ester groups in an alkaline or acidic aqueous medium. The hydrolysis can be carried out in an aqueous solution or suspension of the compounds of formula Ic in the presence of acid or alkali, optionally diluted with a solvent which is inert under the reaction conditions. Acids which can be used include aqueous solutions of organic or inorganic acids. Organic acids suitable for this purpose include lower alkane carboxylic acids such as formic acid, acetic acid etc., haloalkane carboxylic acids such as chloroacetic acid or organic sulfonic acids such as p-toluenesulfonic acid. Suitable inorganic acids include mineral acids such as hydrochloric acid or phosphoric acid. Alkalis which can be used include aqueous solutions or suspensions of oxides, hydroxides or carbonates of alkali metals or alkaline earth metals. The hydrolysis of the esters of formula Ic is advantageously carried out under alkaline reaction conditions using aqueous alkali metal hydroxides. The hydrolysis is preferably carried out with aqueous sodium hydroxide solution. It is possible and preferable to employ the methoxy ($R^4=CH_3$) or ethoxy ($R^4=C_2H_5$) ester as compound Ic. The esters of formula Ic can be converted into compounds of formula Id at temperatures between room temperature and the boiling point of the solvent, where appropriate removing the alcohol which forms in this reaction by distillation.

The preparation of compounds of formula Id by process variant c) can be carried out by reacting reactive acid derivatives of formula III in which U represents a reactive radical with amines of formula IV by conventional peptide chemistry methods for forming amide groups by aminoacylation.

Particularly suitable reactive derivatives of formula III include acid halides, preferably chlorides, esters and mixed anhydrides, for example compounds of formula III in which the reactive group U denotes halogen, especially chlorine or bromine, lower alkoxy, especially alkoxy with 1 to 4 carbon atoms, or a group O-W in which W represents a lower alkylcarbonyl or lower alkoxycarbonyl group or an organic sulfonic acid radical, especially the radical of a lower alkanesulfonic acid such as, for example, methanesulfonic acid or of an aromatic sulfonic acid such as benzenesulfonic acid or benzenesulfonic acids substituted by lower alkyl or halogen. It is also possible to start from the base acid of formula III (U=OH) of the reactive acid derivative itself. Before the actual reaction with the amine of formula IV, the acid is first converted in situ by known methods into the reactive acid derivative which is subsequently used without further isolation or purification, for reaction with the amine of formula IV. The in situ formation of the reactive acid derivative can advantageously be carried out at temperatures from $-30°$ C. to room temperature using solvents such as halogenated hydrocarbons, ethers, preferably cyclic ethers such as tetrahydrofuran, and/or aromatic solvents.

Acid halides, especially acid chlorides, or mixed acid anhydrides, especially mixed anhydrides obtained from reaction of the base acids of formula III (U=OH) with an organic sulfonyl chloride such as methane sulfonyl chloride or with chloroformate esters, are preferably used as compounds of formula III. In a preferred procedure acid derivatives are used which, before the actual reaction, were first prepared in situ from the base acid of formula III (U=OH) and which are reacted without previous isolation or purification, directly with the amine of formula IV to form an amide. The reaction of the amine IV with the acid halide or anhydride of formula III is carried out in the presence of an inert organic solvent, for example a halogenated hydrocarbon such as methylene chloride, a cyclic or open ether such as dioxane or diethyl ether, dimethylformamide, sulfolane, tetramethylurea or mixtures of these solvents and, where appropriate, aromatic hydrocarbons such as benzene or toluene. Where acid halides or anhydrides of formula III are used, it is advantageous to carry out the reaction in the presence of an acid-binding agent. Suitable acid-binding agents include inorganic bases, for example alkali metal carbonates, or alkali metal hydroxides or organic bases, especially tertiary lower alkylamines, for example triethylamine or pyridines. It is also possible to use an excess of the amine of formula IV in place of an alien base. Organic bases used in excess can also simultaneously act as solvent. It may furthermore be advantageous to add catalytic amounts of basic pyridines such as 4-dimethylaminopyridine or 4-pyrrolidinopyridine. The reaction is advantageously carried out at temperatures between $-30°$ C. and the boiling point of the reaction mixture. The chosen temperature can vary depending on the starting compounds used, for example when acid halides or anhydrides of formula III are used, low temperatures up to about room temperature, especially temperatures from about $-20°$ C. to $0°$ C., are preferred. It is especially advantageous to react a solution of the acid derivative of formula III at a very low temperature with a solution of the amine of formula IV.

Process variant c) is particularly suitable for reacting compounds of formula III in which $Z^1$ and $Z^2$ represent alkoxy or together represent alkylenedioxy, or $Z^1$ represents alkoxy and $Z^2$ together with Y represents a bond. However, keto compounds of formula III ($Z^1$ and $Z^2$ together=oxygen) can also be reacted with amines of formula IV to yield compounds of formula Id.

In process variant d) the compounds of formula V undergo hydrolytic cleavage. This hydrolytic cleavage of the enamide compounds of formula V can be carried out by conventional peptide chemistry methods for cleaving enamide groups. The hydrolysis of the enamide compounds of formula V is advantageously carried out in an aqueous medium under acidic reaction conditions, where appropriate in the presence of a water-miscible organic solvent. Examples of suitable solvents include lower alcohols, acetone or cyclic ethers such as dioxane or furan, preferably lower alcohols such as methanol or ethanol. It is possible and desirable to employ compounds of formula V in which $R^{12}$ represents trifluoromethyl. The enamide group can be cleaved straightforwardly by treatment with an aqueous solution of an organic or inorganic acid. Suitable organic acids include lower alkane carboxylic acids such formic acid, acetic acid etc. or halocarboxylic acids such as chloroacetic acid. Examples of suitable inorganic acids include hydrochloric acid or phosphoric acid. Aqueous mineral acids, especially hydrochloric acid, are preferably used. The hydrolysis of the enamide compounds can be carried out at temperatures between room temperature and the boiling point of the solvent.

The reaction of the acids of formula Ib or their reactive acid derivatives with amines of formula VI by process variant e) can be carried out by conventional peptide chemistry methods for forming amide groups by aminoacylation, for example under the conditions indicated above for reacting a compound of formula III with a compound of formula IV. Process variant e) is particularly suitable for reacting compounds of formula Ib in which $Z^1$ and $Z^2$ represent alkoxy or together represent alkylenedioxy, or $Z^1$ represents alkoxy and $Z^2$ together with Y represents a bond. However, keto compounds of formula Ib ($Z^1$ and $Z^2$ together=oxygen) can also be reacted with amines of formula VI to give compounds of formula If.

If, in the amine of formula VI used, $R^5$ represents hydrogen and $R^6$ represents the deamino radical of a biogenic α-amino carboxylic acid, it is advantageous for the free carboxyl group contained therein to be provided, before the above reactions, in a known manner with a protective group which can easily be removed again afterward. Suitable protective groups are known, for example, from E. McOmie, "Protective Groups in Organic Chemistry", Plenum Press (1971). For example, ester groups such as, for example, methyl ester, benzyl ester, p-nitrophenyl esters etc. are suitable for protecting carboxyl groups present in amino carboxylic acids.

Where the deamino radical of the amino carboxylic acid contains further functional groups in addition to the carboxyl group, these can also be provided where appropriate with protective groups during the foregoing reactions.

The compounds of formula I can be isolated from the reaction mixture and purified in a known manner. Salts of acids of formula I can be converted in a customary manner into the free acids, and the latter can, if desired, be converted in a known manner into pharmacologically acceptable salts of these acids. The pharmacologically acceptable salts of acids of formula I with metal cations and ammonium ions of formula C are prepared by customary methods of salt formation.

Salts with metal cations are obtained, for example, by dissolving the acids of formula I in a water-miscible organic solvent, in particular in a lower alcohol such as methanol or ethanol; reacting with solid, powdered metal hydroxide or with a solution or suspension of the oxide or hydroxide of the metal cation in water, and subsequently isolating and purifying the corresponding metal salt of the acid in a known manner. For example, some salts of acids of formula I with metal cations crystallize out of the reaction solution even at room temperature, it being possible to complete the crystallization by additional cooling to about $4°$ C. Other salts of acids of formula I with metal cations can be precipitated out of the reaction solution by addition of suitable solvents, for example organic solvents which are miscible with water, such as ethyl acetate or acetone or other ketones, or hydrocarbons, such as petroleum ether or hexane, optionally with cooling where appropriate.

Salts of acids of formula I with ammonium ions of formula C are obtained, for example, by dissolving the acid in a water-miscible organic solvent, particularly a lower alcohol, acetone or ethyl acetate, and adding dropwise an amine on which the ammonium group C is based or an ammonium salt containing the ammonium group C dissolved in an organic solvent such as a halogenated hydrocarbon, particularly methylene chloride, or a hydrocarbon, particularly hexane. In particular, if a salt of an acid of formula I with a cation of a basic amino acid ($R^8$, $R^9$ and $R^{10}$=hydrogen, and $R^{11}$=a deamino radical of the basic amino acid) is desired, it can be obtained, for example, by dissolving the acid in a water-miscible organic solvent, particularly a lower alcohol such as methanol; reacting with a solution of the basic amino acid in a lower alcohol, particularly methanol, and subsequently isolating and purifying the corresponding salt of the acid with the basic amino acid in a known manner. In some cases salts of acids of formula I with basic amino acids crystallize out of the reaction solution even at room temperature. Otherwise, salts of acids of formula I with basic amino acids can also be precipitated out of the reaction solution by adding suitable solvents, for example water-miscible solvents such as ethyl acetate or acetone or other ketones, optionally with additional cooling.

The starting materials for preparing the compounds of formula I can be obtained by known processes.

The ketal and enol ether compounds of formula II to be used in process variant a) can be obtained by reacting an acid or an acid derivative of formula VII

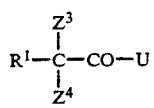   VII in which $Z^3$ and $Z^4$ have the above meanings, and U represents hydroxy or a reactive radical, with an amine of formula IV by conventional peptide chemistry methods for forming amide groups by aminoaoylation, for example under the conditions indicated above for reacting a compound of formula III with a compound of formula IV.

Compounds of formula VII can be prepared by ketalization of the base α-keto acid compounds of formula IIIa

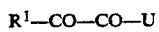   IIIa in which $R^1$ and U have the above meanings, by conventional methods. For example, the ketalization may be carried out under catalysis by anhydrous organic or inorganic acids by reacting an α-keto acid or derivative thereof with an alcohol, alkylenediol, thiol or alkylene dithiol. The water formed in the ketalization reaction with alcohols or alkylenediols may be trapped by water-binding agents, for example with dialkyl sulfites in the preparation of dialkyl oxoketals. The water formed in the reaction can also be removed by azeotropic distillation. It is also possible to use corresponding trialkyl orthoformates, for example trimethyl or triethyl orthoformate, in place of the alcohols as ketalizing agents.

The amines of formula IV are known or can be prepared in a known manner from the base amino acid by conventional methods for forming esters or amides.

The compounds of formula III for use in process variant c) can be obtained by conventional methods. The keto acids of formula IIIa (U=OH) are known or can be obtained in a known manner, for example by first reacting the base amino acid of formula XIIIa

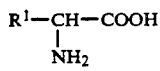   XIIIa in which $R^1$ has the above meaning, with trifluoroacetic anhydride (formula XIV, $R^{12}=CF_3$) to give the 4-substituted 2-trifluoromethyl-5-oxazolone of formula XIa,

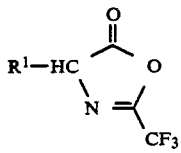   XIa in which $R^1$ has the above meaning, by heating either without a solvent or else in the presence of a solvent such as, for example, methylene chloride. The resulting oxazolone of formula XIa can subsequently be converted into the keto acid of formula IIIa by basic hydrolysis, during which an intramolecular oxidation-reduction reaction simultaneously occurs. Alkalis such as, for example, sodium or potassium hydroxide are suitable for this hydrolysis reaction. To convert the amino acid isoleucine ($R^1=-CH(CH_3)CH_2CH_3$ in formula XIIIa) into the corresponding keto acid, it is advantageous to carry out the hydrolysis of the corresponding oxazolone ($R^1=-CH(CH_3)CH_2CH_3$ in formula XIa) in a buffer at about pH=6.8 in order to avoid racemization of the asymmetric carbon atom present in the isoleucine radical $R^1=-CH(CH_3)CH_2CH_3$.

The acids of formula IIIa can be converted into their reactive derivatives in a known manner. Ketals and enol ketals of formula III ($Z^1$ and $Z^2$ each=alkoxy or together=alkylenedioxy, or $Z^1$=alkoxy and $Z^2$ together with Y=a bond) can be prepared by ketalization of the base keto compounds of formula IIIa with alcohols or alkylenediols by conventional methods, for example under the conditions described for preparing compounds of formula VII.

The starting compounds of formula V for use in process variant d) can be obtained by reacting substituted, unsaturated oxazolones of formula VIII

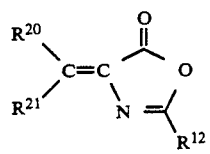   VIII in which $R^{20}$, $R^{21}$ and $R^{12}$ have the above meanings, with amines of formula IV. The reaction of a compound of formula VIII with a compound of formula IV is carried out under conditions customary in peptide chemistry, for example under the conditions described above for reacting a compound of formula III with a compound of formula IV.

Two routes are available for preparing oxazolones of formula VIII. The first way to prepare unsaturated oxazolones of formula VIII starts from keto compounds of formula IX

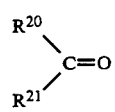   IX in which $R^{20}$ and $R^{21}$ have the above meanings. These are condensed with N-acylglycine derivatives of formula X

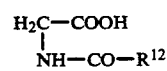   X in which $R^{12}$ has the above meaning, in a known manner (Erlenmeyer synthesis). For this, for example, a compound of formula IX is reacted with a compound of formula X in a suitable solvent such as, for example methanol, with the addition of a tertiary base such as pyridine or in the presence of sodium acetate and acetic anhydride. The condensation can be carried out at temperatures between room temperature and the boiling point of the solvent.

The second way of preparing unsaturated oxazolones of formula VIII starts in a known manner from substituted, saturated oxazolones of formula XI

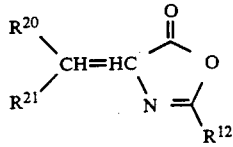

in which $R^{20}$, $R^{21}$ and $R^{12}$ have the above meanings. These are first halogenated, preferably brominated, to give compounds of formula XII

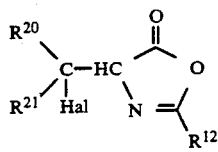

in which $R^{20}$, $R^{21}$ and $R^{12}$ have the above meanings, and Hal represents halogen, preferably bromine. The halogenation of compounds of formula XI is carried out under know conditions by reacting a compound of formula XI in a solvent which is inert under the reaction conditions, for example 1,2-dichloroethane, with the halogen, preferably bromine, to yield a compound of formula XII. The halogenated derivatives XII are subsequently dehydrohalogenated by treatment with an organic base, preferably triethylamine, to yield the unsaturated oxazolones of the formula VIII. For this purpose a compound of formula XII can be reacted in a known manner in a solvent which is inert under the reaction conditions, such as an ether, for example a cyclic ether such as tetrahydrofuran, by treatment with a tertiary organic base, preferably triethylamine, to yield a compound of formula VIII.

The oxazolones of formula XI can be prepared in a known manner, for example by reacting an α-amino carboxylic acid of formula XIII

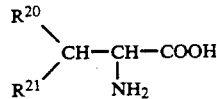

in which $R^{20}$ and $R^{21}$ have the above meanings, by heating with an acid anhydride of formula XIV

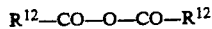

in which $R^{12}$ has the above meaning, optionally diluting with a solvent which is inert under the reaction conditions; or, for example, by reacting an N-acylated α-amino carboxylic acid of formula XV

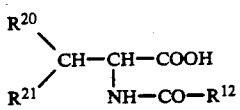

in which $R^{20}$, $R^{21}$ and $R^{12}$ have the above meanings, with an inorganic acid halide such as phosphorus trichloride, phosphorus pentachloride, phosphorus oxychloride or thionyl chloride, preferably phosphorus oxychloride, in the presence of a tertiary organic base such as, for example, pyridine, optionally diluting with a solvent which is inert under the reaction conditions; or, for example, by reacting an N-acylated α-amino carboxylic acid of formula XV with isopropylmethyl chloroformate in the presence of a tertiary organic base such as triethylamine, optionally diluting with a solvent which is inert under the reaction conditions.

In a special variant for preparing enamide compounds of formula V by reacting an unsaturated substituted oxazolone of formula VIII with an amine of formula IV, the unsaturated oxazolone of formula VIII can also be formed in situ from the corresponding brominated oxazolone of formula XII. For this purpose, a compound of formula XII is added directly to a solution of the amine IV and of a tertiary organic base such as, for example, triethylamine.

The following examples are intended to illustrate the preparation of the new compounds of formula I in detail without restricting the scope of the invention in any way.

The structures of the new compounds were verified by elemental analysis and spectroscopic investigations, in particular by analysis of the NMR, mass and/or IR spectra.

EXAMPLE 1

Ethylene ketal of ketoleucylleucine methyl ester a) Ten g of ketoleucine were reacted with 16.7 g of ethylene glycol with the addition of 0.15 g of p-toluenesulfonic acid in 160 ml of toluene at the boiling point for 16 hours, during which the water that formed in the reaction was continuously removed from the reaction mixture by distillation and collected in a water trap. After the reaction was complete, the reaction mixture was washed with water and dried over sodium sulfate. The toluene solvent was subsequently removed under reduced pressure. 16.8 g of the ethylene ketal of ketoleucylglycol ester were obtained as residue.

b) A solution of 16.0 g of the ethylene ketal of ketoleucylglycol ester obtained in step a) in 100 ml of methanol was, after addition of 91.5 ml of a 2N sodium hydroxide solution, stirred at room temperature for 1 hour. The methanol solvent was subsequently removed under reduced pressure, and the remaining aqueous solution was adjusted to pH 1 with concentrated hydrochloric acid. After the acidic solution had been stirred for 15 minutes, the free acid of the ethylene ketal of ketoleucine which had formed was extracted with methylene chloride, and the methylene chloride extract was dried over sodium sulfate. Removal of the methylene chloride solvent under reduced pressure yielded 11.4 g of the ethylene ketal of ketoleucine.

c) 11.4 g of the ethylene ketal of ketoleucine obtained under b) and 8.7 g of dimethylaminopyridine were dissolved in 600 ml of tetrahydrofuran and, after addition of 13.2 g of triethylamine, cooled to −20° C. Subsequently, at this temperature, a solution of 8.2 g of mesyl chloride (methylsulfonyl chloride) in 25 ml of tetrahydrofuran was added dropwise, resulting in a solution of a derivative activated at the acid group of the ethylene ketal of ketoleucine. To this solution was added, for peptide formation, 11.8 g of leucine methyl ester hydrochloride, after which the reaction mixture was warmed to room temperature.

To isolate the peptide derivative which formed in this reaction, the precipitates which had formed were filtered out with suction, and the solvent was removed under reduced pressure. The remaining oily residue was dissolved in methylene chloride and washed with water, and the resulting methylene chloride solution was then dried over sodium sulfate. Removal of the methylene chloride under reduced pressure left an oily product which was purified by column chromatography (silica gel; mobile phase hexane/ethyl acetate 2:1). 18.4 g of the ethylene ketal of ketoleucylleucine methyl ester were isolated in the form of a yellow oil.

The infrared spectrum (film) of the product compound had absorption bands at the following wave numbers (in $cm^{-1}$): 1740, 1680, 1520.

EXAMPLES 2–4

The ethylene ketals listed in Table 1 were prepared by procedures analogous to Example 1.

TABLE 1

| Example | Ethylene ketal of | IR data |
|---|---|---|
| 2 | Ketoleu—Val—OMe | 1740 |
|  |  | 1720 |
|  |  | 1670 |
|  |  | 1520 |
| 3 | Ketoval—Leu—OMe | 1740 |
|  |  | 1680 |
|  |  | 1515 |
| 4 | Ketoval—Val—OMe | 1740 |
|  |  | 1650 |
|  |  | 1530 |

EXAMPLE 5

Ethylene ketal of ketoleucylleucine 240 mmol of sodium hydroxide in the form of an aqueous 2N sodium hydroxide solution were added to a solution of 18.4 g of the ethylene ketal of ketoleucylleucine methyl ester obtained in Example 1 in 50 ml of methanol, and the reaction solution was stirred at room temperature for 2 hours. Removal of the solvent under reduced pressure yielded the crude title compound in the form of its sodium salt.

Although the crude product obtained in this way can be converted into the free acid and subsequently purified, it can also be used directly for further reactions.

EXAMPLE 6

Ketoleucylleucine

The crude product obtained in Example 5 was adjusted to pH 1 with concentrated hydrochloric acid, and the resulting mixture was stirred for 15 minutes. It was subsequently extracted with methylene chloride, and the methylene chloride extract was dried over sodium sulfate. Removal of the methylene chloride solvent under reduced pressure and purification of the residue by column chromatography (silica gel; mobile phase hexane/ethyl acetate 1:1) resulted in 12.2 g of ketoleucylleucine in the form of the free acid as a pale yellow oil.

The infrared spectrum (film) of the prepared compound exhibited absorption bands at the following wave numbers (in $cm^{-1}$): 1720, 1710, 1670, 1530. The following resonances were found in the $^{13}C$—NMR spectrum (in ppm): 201.5; 160.0; 57.2; 175.5.

EXAMPLES 7–9

The free ketodipeptide acids shown in the following Table 2 were obtained by procedures analogous to Examples 5 and 6.

TABLE 2

| Example | Product | IR Data ($cm^{-1}$) | $^{13}C$-NMR Data (ppm) | Notes |
|---|---|---|---|---|
| 7 | Ketoleu—Val | 1733 | 197.9 | Melting |
|  |  | 1718 | 160.3 | point |
|  |  | 1661 | 57.2 | 174–178° C. |
|  |  | 1539 | 175.7 |  |
| 8 | Ketoval—Leu | 1720 |  |  |
|  |  | 1710 |  |  |
|  |  | 1650 |  |  |
|  |  | 1525 |  |  |
| 9 | Ketoval—Val | 1710 | 201.5 |  |
|  |  | 1660 | 160.0 |  |
|  |  | 1550 | 57.2 |  |
|  |  |  | 175.5 |  |

EXAMPLE 10

Ketovalylleucine methyl ester a) 44 ml of concentrated hydrochloric acid were added to a solution of 20.0 g of the calcium salt of ketovaline in 100 ml of distilled water, and the mixture was stirred for 20 minutes. The mixture was subsequently extracted with dichloromethane, and the collected organic phases were dried over sodium sulfate. Removal of the solvent under reduced pressure left 13.1 g of ketovaline in the form of the free acid.

b) 15.1 g of dimethylaminopyridine were added to a solution of 13.0 g of the ketovaline obtained in step a) in 100 ml of tetrahydrofuran. While stirring, 22.7 g of triethylamine were added dropwise, and the reaction mixture was cooled to $-20°$ C. Subsequently a solution of 14.1 g of mesyl chloride in 50 ml of tetrahydrofuran was added dropwise, and the mixture was stirred for a further 20 minutes. Then a solution of 20.4 g of leucine methyl ester hydrochloride in 150 ml of dichloromethane was added dropwise, and the mixture was again stirred for 20 minutes. The mixture was then allowed to warm slowly to room temperature, undissolved constituents were separated by filtration, and the solvent was removed from the filtrate under reduced pressure. The residue was taken up in distilled water and extracted with dichloromethane. The collected organic phases were then dried over sodium sulfate and, after filtration, the solvent was removed under reduced pressure. 14.7 g of the title compound remained as a yellow oil.

The infrared spectrum (film) of the prepared compound exhibited absorption bands at the following wave numbers (in $cm^{-1}$): 1740, 1720, 1685, 1520.

EXAMPLE 11

Ketovalylleucine 113.5 ml of a 2N sodium hydroxide solution were added to a solution of 22.1 g of the ketovalylleucine methyl ester obtained in Example 10 in 200 ml of methanol, and the mixture was stirred for 1 hour. The methanol solvent was subsequently removed under reduced pressure, and the resulting aqueous solution was buffered with saturated ammonium chloride solution. After the mixture had been adjusted to pH 2 with 6N hydrochloric acid, it was extracted with dichloromethane. The collected organic phases were dried over sodium sulfate, and after filtration, the solvent was removed under reduced pressure. 15.0 g of the title compound were obtained in the form of an oil. The compound proved to have properties identical to those of the product obtained in Example 8.

EXAMPLE 12

Ketoisoleucylleucine

Ketoisoleucylleucine was prepared by a procedure analogous to Examples 10 and 11. The title compound was obtained in the form of an oil. The resulting compound had bands at the following wave numbers (in cm$^{-1}$) in the IR spectrum (film): 1725, 1710, 1680, 1540.

Ketoleucylleucine, ketoleucylvaline and ketovalylvaline were also prepared by procedures analogous to Examples 10 and 11. These compounds proved to have properties identical to those of the corresponding products obtained in Examples 6, 7 and 9, respectively.

EXAMPLE 13

Ketovalylvaline methyl ester a) 314 mmol of triethylamine were added to a solution of 46.4 g of valine methyl ester hydrochloride in 500 ml of tetrahydrofuran, and the mixture was then stirred for 15 minutes. Subsequently a solution of 73.9 g of α-bromooxazolone in 750 ml of tetrahydrofuran was added, and the mixture was then stirred at room temperature for 24 hours. The solvent was subsequently removed under reduced pressure, the residue was taken up in ethyl acetate, and the solution was washed twice with water and once with dilute hydrochloric acid. The ethyl acetate solution was subsequently dried over sodium sulfate, and then the solvent was removed under reduced pressure. Recrystallization of the remaining residue from methanol/water resulted in 95.4 g of N-trifluoroacetyldehydrovalylvaline methyl ester as yellowish-white crystals with a melting point of 152°-155° C.

b) 70 ml of 4N hydrochloric acid were added to a solution of 10.0 g of the N-trifluoroacetyldehydrovalylvaline methyl ester obtained in step a) in 80 ml of methanol, and the mixture was heated under reflux for 3 hours. The solvent was then removed under reduced pressure, and the remaining residue was neutralized with dilute sodium hydroxide solution and extracted with dichloromethane. The dichloromethane extract was dried over sodium sulfate. Removal of the dichloromethane solvent under reduced pressure yielded 6.5 g of ketovalylvaline methyl ester in the form of a yellow oil.

The infrared spectrum (film) of the prepared compound exhibited absorption bands at the following wave numbers (in cm$^{-1}$): 1740, 1720, 1680, 1510.

The compounds shown in the following Table 3 were prepared by procedures analogous to Example 13.

TABLE 3

| Example | Product | IR data (cm$^{-1}$) | $^{13}$C-NMR Data (ppm) | Notes |
| --- | --- | --- | --- | --- |
| 14 | Ketoval—Leu—OMe | 1740 1720 1685 1520 | | Substance properties identical to product obtained in Example 10 |
| 15 | Ketoleu—Leu—OMe | 1740 1715 1660 1550 | 198.2 160.0 51.0 170.7 | |

EXAMPLE 16

Diethylamide of ketoleucylleucine

A solution of 5.8 g of ketoleucylleucine methyl ester obtained in Example 15 and 1 g of ammonium chloride in 20 ml of diethylamine was heated under reflux for 1.5 hours. The reaction mixture was then taken up in water/methylene chloride, and the organic phase was separated, washed twice with water and subsequently twice with 0.1N hydrochloric acid, and then dried over sodium sulfate. Removal of the solvent under reduced pressure yielded 3.9 g of the title compound as a yellow oil.

The resulting compound showed bands at the following wave numbers (in cm$^{-1}$) in the IR spectrum (film): 1720, 1660, 1650, 1540.

EXAMPLE 17

Calcium salt of ketoleucylleucine 2.9 g of calcium hydroxide were added to a solution of 19.1 g of the ketoleucylleucine obtained in Example 2 in 100 ml of methanol, and the mixture was briefly heated under reflux. After addition of ethyl acetate to the cooled reaction solution, 15 g of the calcium salt of ketoleucylleucine crystallized out in the form of a colorless crystalline solid with a melting point of 236 to 237° C.

The resulting compound showed the following resonances in the $^{13}$C—NMR spectrum (in ppm): 198.8; 160.3; 52.9; 180.1.

EXAMPLE 18

Calcium salt of ketoisoleucylleucine

The ketoisoleucylleucine obtained in Example 12 was converted into the calcium salt by a procedure analogous to Example 17. The crystalline title compound was obtained having a melting point of 232°-236° C.

The resulting compound showed bands at the following wave numbers (in cm$^{-1}$) in the IR spectrum (KBr): 1715, 1650, 1550, 1405.

EXAMPLE 19

Magnesium salt of ketoleucylleucine

A suspension of 3.4 g of magnesium hydroxide in 150 ml of water was added to a solution of 28.5 g of the ketoleucylleucine obtained in Example 2 in 300 ml of methanol, and the mixture was heated under reflux for 2 hours. After the mixture had been slowly cooled to room temperature, it was stirred while cooling with an ice bath for 1 hour. The crystallized colorless product was filtered out with suction, washed with water and subsequently dried. 17.6 g of the title compound were obtained with a melting point of 271° C.

The prepared compound showed the following resonances in the $^{13}$C—NMR spectrum (in ppm): 199.3; 161.9; 54.2; 179.1.

EXAMPLE 20

Sodium salt of ketoleucylleucine

A solution of 8.3 g of the ketoisoleucylleucine obtained in Example 2 in 150 ml of ethanol was adjusted to pH 7 with aqueous 1N sodium hydroxide solution. Subsequently petroleum ether was added until inception of turbidity, and the mixture was then stirred while cooling with an ice bath for 2 hours. The precipitated product was filtered out with suction, washed with diethyl ether, and dried over phosphorus pentoxide in vacuo. 4.4 g of the highly hygroscopic title compound were obtained with a melting point above 200° C.

The prepared compound showed the following resonances in the: $^{13}C$—NMR spectrum (in ppm): 200.2; 162.0; 53.9; 178.7.

EXAMPLE 21

Bis-ornithate of ketoleucylleucine

A solution of 16.2 g of the basic amino acid 15 ornithine in 200 ml of methanol was added to a solution of 28.9 g of the ketoleucylleucine obtained in Example 2 in 300 ml of methanol, and the mixture was briefly heated under reflux. Subsequently ethyl acetate was added to the solution at the boiling point until inception of turbidity. After slow cooling to room temperature it was stirred while cooling with an ice bath for 1 hour. The precipitated product was filtered out with suction, washed with ethyl acetate and subsequently dried. 26.6 g of the title compound which contained ketoleucylleucine and ornithine in the molar ratio 1:2 were obtained in the form of a colorless crystalline salt with a melting point of 134° to 139° C.

The compound exhibited the following resonances in the $^{13}C$—NMR spectrum (in ppm): 200.8; 162.5; 54.5; 179.6.

EXAMPLES 22 AND 23:

The crystalline salts of ketodipeptides with the basic amino acid lysine which are shown in the following Table 4 were prepared by a procedure analogous to Example 21.

TABLE 4

| Example | Lysinate of | IR data (cm$^{-1}$) | Melting point | Molar ratio ketodipeptide to lysine |
| --- | --- | --- | --- | --- |
| 22 | Ketoleu—Leu | 1735 1720 1675 1520 | 167° C. | 1:1.25 |
| 23 | Ketoval—Val | 3400 1720 1710 1680 1510 1400 | 179–181° C. | 1:1 |

EXAMPLE 24

Infusion solution as supplement for parenteral nutrition regimes

To prepare a solution which can be administered parenterally, ketoisoleucylleucine in the form of the calcium or ornithine salt and ketovalylvaline in the form of the lysine salt were dissolved while stirring in distilled water (for injections), care being taken that atmospheric oxygen was substantially excluded by introducing nitrogen. The solution was pumped through a series of filters with a final filter of 0.2 μm pore diameter to remove particles and reduce the microbe count. Sufficient amounts of the ketoisoleucylleucine and ketovalylvaline salts were used to provide the following concentrations in the finished solution calculated on the basis of the free ketodipeptide acids corresponding to the salts which were used:

CO—Ile—Leu 10.95 g/100 ml, and
CO—Val—Val 7.53 g/10 ml.

The resulting solutions having this composition were suitable for parenteral administration as a parenteral nutrition supplement. Thus, they were packaged by dispensing them directly into rinsed glass bottles; the headspaces of the filled glass bottles were evacuated, and the glass bottles were thereafter sealed with rubber stoppers and crimp-capped. The sealed and crimp-capped glass bottles were subsequently sterilized in an autoclave at 121° C. for 8 minutes.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A compound corresponding to the formula I:

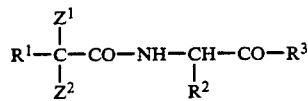

in which
$R^1$ represents an organic radical A

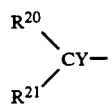

in which
Y represents hydrogen or together with $Z^2$ another bond, $R^{20}$ represents hydrogen or methyl, and if $R^{20}$ is hydrogen, $R^{21}$ denotes isopropyl or, if $R^{20}$ is methyl, $R^{21}$ denotes methyl or ethyl, $R^2$ represents an organic radical A'

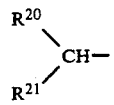

in which
$R^{20}$ and $R^{21}$ have the above meanings,
$R^3$ represents hydroxy or lower alkoxy or an amino group B

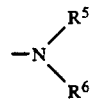

in which
$R^5$ denotes hydrogen or lower alkyl, and
$R^6$ denotes hydrogen, lower alkyl or, if $R^5$ is hydrogen, the deamino radical of a biogenic L-α-amino carboxylic acid, or
$R^5$ and $R^6$ together with the N atom to which they are bonded form a saturated heterocycle selected from the group consisting of aziridine, pyrrolidine and piperidine, and $Z^1$ and $Z^2$ together represent oxygen or a physiologically acceptable alkylenedioxy group O—(CH$_2$)$_n$—O in which n is 1 to 4, or $Z^1$ and $Z^2$ each represent a physiologically acceptable $R^7$—O— group in which $R^7$ denotes lower alkyl, or $Z^1$ represents an $R^7$—O— group in which $R^7$ has the above meaning, and $Z^2$ together with Y represents a bond, or a salt thereof in which $R^3$ represents hydroxy with a physiologically acceptable cation.

2. A compound according to claim 1, wherein $Z^1$ and $Z^2$ together represents oxygen, and Y represents hydrogen.

3. A compound according to claim 1, wherein $Z^1$ and $Z^2$ together represents oxygen or a physiologically acceptable alkylenedioxy group O—$(CH_2)_n$—O in which n is 1 to 4, or $Z^1$ and $Z^2$ each represent a physiologically acceptable $R^7$—O— group in which $R^7$ denotes lower alkyl, and Y represents hydrogen.

4. A compound according to claim 3, wherein $Z^1$ and $Z^2$ each represent an ethoxy group.

5. A compound according to claim 1, wherein $R^1$ represents an organic radical A in which $R^{20}$ denotes hydrogen and $R^{21}$ denotes isopropyl, or $R^{20}$ and $R^{21}$ each denote methyl.

6. A compound according to claim 1, wherein $R^2$ represents an organic radical A' in which $R^{20}$ denotes hydrogen and $R^{21}$ denotes isopropyl, or $R^{20}$ and $R^{21}$ each denote methyl.

7. A compound according to claim 2, wherein $R^1$ and $R^2$ each independently represent an organic radical corresponding to the formula:

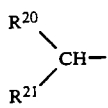

in which $R^{20}$ denotes hydrogen and $R^{21}$ denotes isopropyl, or in which $R^{20}$ and $R^{21}$ each denote methyl.

8. A compound according to claim 1, wherein $R^3$ represents hydroxy or a salt thereof with a physiologically acceptable cation.

9. A compound according to claim 8, wherein said cation is selected from the group consisting of physiologically acceptable metal cations and physiologically acceptable ammonium groups C

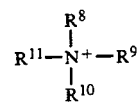

in which $R^8$, $R^9$, $R^{10}$ and $R^{11}$ each independently represent hydrogen or lower alkyl, or two of the substituents $R^8$ to $R^{11}$ together denote a $C_4$ or $C_5$ alkylene chain and the other substituents each denote hydrogen, or one of the substituents $R^8$ to $R^{11}$ represents a deamino radical of a basic biogenic L-α-amino carboxylic acid and the other substituents each denote hydrogen.

10. A compound according to claim 9, wherein said cation is a physiologically acceptable metal cation selected from the group consisting of sodium, potassium, calcium, magnesium and zinc cations.

11. A compound according to claim 9, wherein said cation represents the ammonium ion $NH_4^+$ or an ammonium ion group C in which $R^8$, $R^9$ and $R^{10}$ each denote hydrogen, and $R^{11}$ denotes the deamino radical of a biogenic basic α-amino carboxylic acid selected from the group consisting of Lys, Arg, His and Orn.

12. A method of parenteral nutrition of a mammal comprising parenterally administering to said mammal a sterile, isotonic infusion solution comprising an effective nutritional amount of a compound corresponding to claim 1, in a physiologically acceptable, liquid infusion solution medium.

13. A pharmaceutical or dietetic composition comprising an amount of a compound according to claim 1, effective to increase blood plasma levels of biogenic L-α-amino carboxylic acids and of α-keto carboxylic acids, and a conventional pharmaceutical carrier or adjuvant.

* * * * *